United States Patent
Goertler

(10) Patent No.: US 6,885,884 B2
(45) Date of Patent: Apr. 26, 2005

(54) METHOD FOR SIMULATING THE USE OF A SYSTEM OPTION FOR A TECHNICAL APPARATUS

(75) Inventor: Georg Goertler, Baiersdorf (DE)

(73) Assignee: Siemens Aktiengesellschaft, München (DE)

(*) Notice: Subject to any disclaimer, the term of this patent is extended or adjusted under 35 U.S.C. 154(b) by 470 days.

(21) Appl. No.: 10/147,607

(22) Filed: May 15, 2002

(65) Prior Publication Data

US 2002/0173944 A1 Nov. 21, 2002

(30) Foreign Application Priority Data

May 16, 2001 (DE) .......................... 101 23 795

(51) Int. Cl.⁷ .............................................. A61B 5/05
(52) U.S. Cl. ........................................ 600/407; 600/437
(58) Field of Search ................................ 600/407–472; 128/916; 705/2; 367/7, 9, 11, 47–49; 434/262, 350, 429

(56) References Cited

U.S. PATENT DOCUMENTS 6,466,813 B1 * 10/2002 Shukla et al. .............. 600/411
6,690,820 B1 * 2/2004 Lees et al. .................. 382/154
6,739,877 B1 * 5/2004 Bailey et al. ................ 434/262
6,741,672 B1 * 5/2004 Gaddipati et al. ............. 378/4
6,765,570 B1 * 7/2004 Cheung et al. ............. 345/420

FOREIGN PATENT DOCUMENTS

| DE | OS 197 15 503 | 10/1998 |
|---|---|---|
| DE | OS 198 34 422 | 2/2000 |
| DE | OS 199 17 102 | 12/2000 |
| EP | 0 840 245 | 5/1998 |
| EP | 1 061 422 | 12/2000 |
| EP | 1 061 423 | 12/2000 |

OTHER PUBLICATIONS

"Besser Planen—mit Rechnerunterstützung," Wieser, Technische Rundschau, vol. 3,/90 (1990) pp. 56–59.

* cited by examiner

Primary Examiner—Ali Imam
(74) Attorney, Agent, or Firm—Schiff Hardin LLP

(57) ABSTRACT

In a method for simulating the use of a system option for a technical apparatus, data from technical apparatuses that relate to the configuration and/or the usage of the apparatuses are collected, are stored in a central data bank, and relationships between collected, stored data and/or between collected, stored and additionally prescribable data are produced. The use of a system option for a technical apparatus is simulated based on the data placed in relationship to one another.

7 Claims, 2 Drawing Sheets

| Device | Type | Systems options / examination possibility | | | Usage Examinations per day / ⌀ Duration in minutes | | | Operating duration in hours | Prescribable data | |
| --- | --- | --- | --- | --- | --- | --- | --- | --- | --- | --- |
| | | SO1 heart/lung | SO2 lung | SO3 head | heart | lung | head | | Acquisition costs | Operating costs per day |
| MR1 | X | • | / | / | 10 / 30 | 6 / 50 | / | 10 | | |
| MR2 | Y | • | / | • | 4 / 30 | / | 12 / 40 | 10 | | |
| MR3 | Z | / | / | • | / | / | 15 / 40 | 10 | | |
| MR4 | X | • | • | / | 10 / 30 | 10 / 30 | / | 10 | | |
| ... | | | | | | | | | | |

FIG 2

METHOD FOR SIMULATING THE USE OF A SYSTEM OPTION FOR A TECHNICAL APPARATUS

BACKGROUND OF THE INVENTION

1. Field of the Invention

The present invention is directed to a method for simulating the use of a system option for a technical apparatus, particularly for medical-technical installations, devices and systems.

2. Description of the Prior Art

Technical installations, devices and systems as well as the software required for their operation usually can be implemented in various configurations, the configurations differing by virtue of higher grade embodiments having, for example, higher-performance hardware components or by virtue of the software required for the operation offering additional software components. Regardless of whether the hardware or the software of a technical apparatus is affected, customers have choices referred to as system options that a customer can select when purchasing the technical apparatus. The use or benefit that the customer expects from the system option is critical for the selection of a system option that involves costs for the customer.

Heretofore, only general characterizations, that cannot be customized to the specific requirements of a customer, can be made regarding the expected use or benefit of a system option for the customer, due to a lack of information. All data for supporting the customer use must be estimated, which can lead to unsatisfactory results under certain circumstances.

SUMMARY OF THE INVENTION

An object of the present invention is to provide a method with which the use of a system option for a technical apparatus can be determined in an information-supported fashion.

This object is inventively achieved in a method wherein data for a technical apparatus are collected that are functionally identical or of the same type with respect to the technical apparatus in question for a particular system option, or that can at least supply an equivalent result. Configuration data of the technical apparatus are collected, meaning data about the hardware and software equipment of the apparatus. Further, workflow data of the technical apparatus and data about the use of the apparatus are collected, i.e. when, to what extent, and which hardware or software components of the apparatus are used by the customer. The collected data are stored in a central data bank, and references between the stored data are produced. Further data, such as acquisition costs or operating costs, can be additionally prescribed that are placed into relationship with the collected data and can be required for simulating the use of a system option. References between the data can, for example, be produced by storage standardized form, for example in tables in the data bank, so that the technical apparatuses can be compared to one another with respect to their system options that, as warranted, are supplemented by the additionally prescribable data, for example, on a daily basis. Various scenarios regarding the use of a system option can be simulated for the technical apparatus on the basis of the data placed into relationship with one another. A customer interested in a technical apparatus thus can have the economic feasibility of a system option calculated on the basis of the existing data and, if used also on the basis of the supplementary data, that are relevant for the customer's purposes. In this way, the customer is provided with an overview of the benefit that can be achieved with a system option or of a workflow improvement associated therewith. Further, the distribution organization of a manufacturer of a technical apparatus can locate potential customers for an existing system option or for a new system option upon using the inventive method based on simulations of the use of system options. Moreover, the development department of a manufacturer of a technical apparatus can interrogate or simulate the employment and the use of certain system options. The marketing department of a manufacturer of a technical apparatus can implement market analyses and develop new marketing strategies based on such simulations. In all instances, the use of individual system options for a technical apparatus can be determined on a clearly better-founded basis by employing data for the simulation that are collected from technical apparatuses already in operation, compared to determinations can be achieved by employing purely estimated data. As used herein, the use or benefit taking the costs of the system option into consideration means all advantages that arise due to the respective system option.

In an embodiment of the invention, the data are collected in automated fashion from one or more technical apparatuses and are stored in the central data bank. The collected data can be filtered, so that only specific types of data are forwarded to the central data bank. This has the advantage that not all data are stored, but only the data required for the simulation are stored therein. An overloading of the data bank with relatively irrelevant data is thus avoided.

In another embodiment of the invention the automated collection of the data ensues via a communication network, for example the Internet, an Intranet or an Extranet. The technical apparatuses from which the data are collected preferably are constantly connected to the communication network and communicate the data to the central data bank at least indirectly on their own or on demand. The collection of the data also can ensue via as point-to-point connections via modem, analog or ISDN routers. In this case, the technical apparatuses are at least indirectly connected via such connections to the data bank, for example via a computer that precedes the data bank.

Preferably the technical apparatus is a medical-technical apparatus, including software systems, for example for hospital or clinic administration or for service jobs in addition to medical-technical installations or devices. The medical-technical installations and devices preferably are high-end installations and devices, for example, a magnetic resonance installation, a computed tomography installation, a C-arm x-ray device or an ultrasound device, that are comparatively expensive in terms of acquisition price and, based on a standard configuration, can be equipped with various system options.

DESCRIPTION OF THE DRAWINGS

FIG. 2 illustrates the storage of collected data in a table in the inventive method.

DESCRIPTION OF THE PREFERRED EMBODIMENTS

Figure 1:
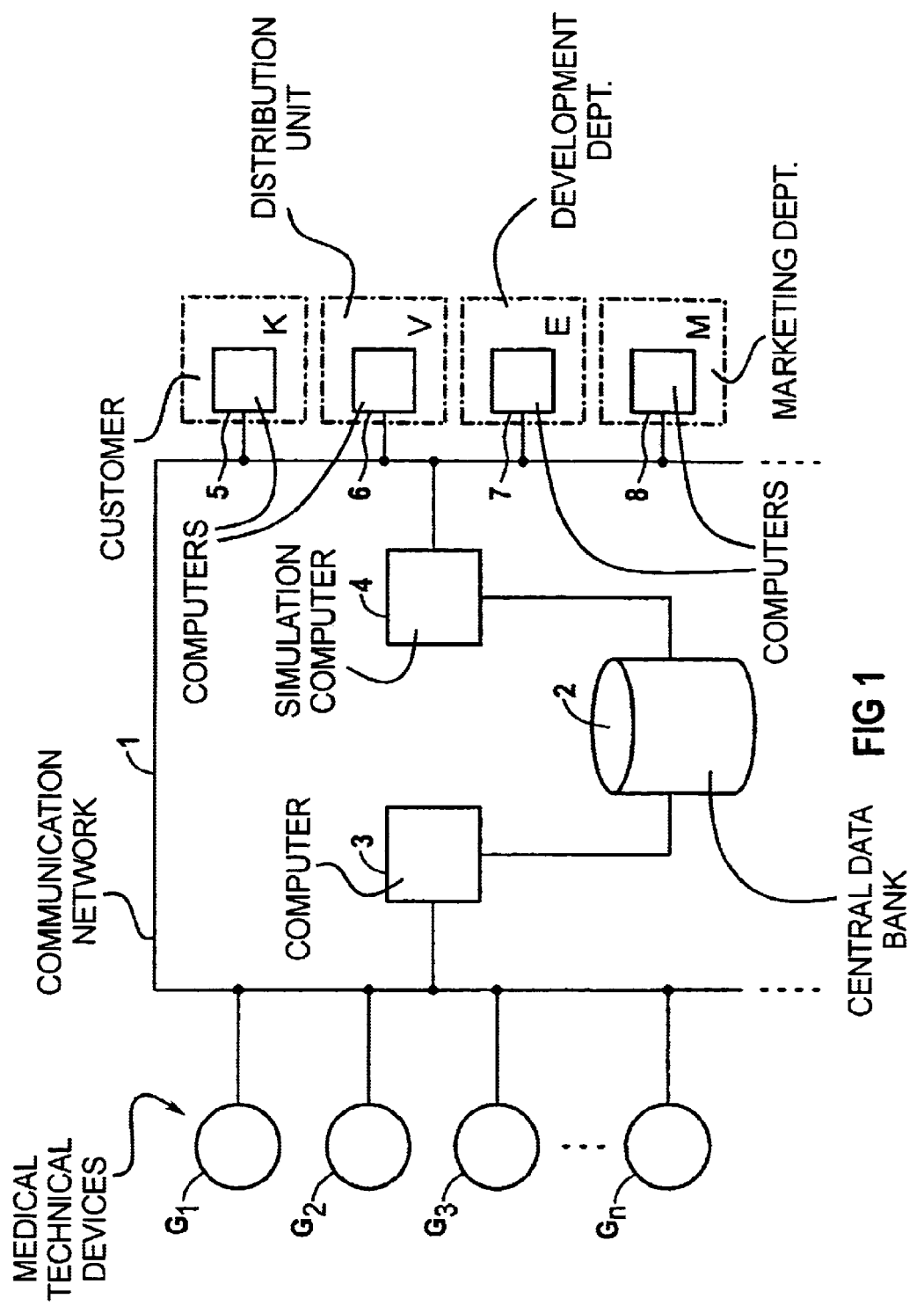
FIG. 1 is a block diagram of a system for implementing the inventive method.

The inventive method is explained below with reference to an example in medical technology. The application of the inventive method, however, is not limited to medical apparatuses.

FIG. 1 shows a medical system that, in the present exemplary embodiment, includes a number of medical-technical apparatuses in the form of medical-technical devices $G_1$ through $G_n$. The devices $G_1$ through $G_n$ are arranged at customers of the manufacturer of the devices, i.e. in clinics, hospitals, physicians' practices and research institutions. In the exemplary embodiment, the devices are magnetic resonance devices, computed tomography installations, C-arm x-ray devices and ultrasound devices. The devices $G_1$ through $G_n$ in the exemplary embodiment are connected to a communication network 1, such as the Internet. The communication network, however, also can be an Intranet or an Extranet.

A first computer 3 connected to a central data bank 2 is connected to the communication network 1. Further, a simulation computer 4 is connected to the data bank 2. This simulation computer 4 has means for data input, for example in the form of a keyboard or a computer mouse, and means for data output, for example in the form of a monitor (not shown but well known).

During the course of the inventive method, the first computer 3 collects data from the devices $G_1$ through $G_n$ in automated fashion via the communication network 1. The collection of the data ensues such that the devices $G_1$ through $G_n$ automatically communicate arising data to the first computer 3 or the first computer 3 can request data from the devices $G_1$ through $G_n$. The communication of the data can ensue at fixed times or whenever new data arise during the operation of the devices $G_1$ through $G_n$.

The data that are collected by the first computer 3 in the exemplary embodiment are configuration data for the devices $G_1$ through $G_n$, including data characterizing the hardware and software equipment of the devices $G_1$ through $G_n$. In the case of a magnetic resonance apparatus, the configuration data included, for example, information about which coils are installed in the magnetic resonance apparatus and with which software components, particularly measurement programs, the magnetic resonance apparatus is equipped. Further, data over the usage of the devices $G_1$ through $G_n$ are collected, particularly about when, how long and for which examinations or treatments hardware or software components of the devices are used by the customer. In the case of a magnetic resonance apparatus, the data, for example, provide information, when various measurements have been carried out, as to which coil was used for which examination, and which protocols or measurement sequences were used. Additionally, workflow data of the devices $G_1$ through $G_n$ are collected that, for example, provide information about the types of patient examinations, for example heart examinations, their frequency, and their time duration.

The data collected by the first computer 3 are subjected to a filtering, so that only specific types of data that are required for the simulation of the use of a system option, proceed into the central data bank 2. The manner by which the data are filtered can be defined in an application-specific context. If all data collected from the devices $G_1$ through $G_n$ can be relevant for the simulation of the use of the system options, the filtering can be foregone, and all data collected from the devices $G_1$ through $G_n$ are stored in the central data bank 2.

The storage of the collected data in the central data bank 2 preferably ensues in a standardized form, in a manner that allows relationships between data that arise from different devices $G_1$ through $G_n$ to be produced by the storage.

In the exemplary embodiment, the storage of the data collected from the devices $G_1$ through $G_n$ ensues in tables that allow an identification as to which devices contain which hardware, and which software system options, as well as which examinations are possible with the devices and which examinations are in fact implemented with the devices.

As an example and in a highly simplified and redacted fashion, FIG. 2 shows such a table for magnetic resonance devices MR1 through MR4 produced for one calendar date. Due to the structure of the table, which provides information about the type of device, the equipment of devices with system options SO1 through SO3, including the examination possibilities that can be implemented therewith, the actual usage of the devices in the form of examinations per day, the average duration per examination in minutes, as well as the operating duration of the devices in hours. The specific data of the magnetic resonance devices MR1 through MR4 have already been placed in relationship with one another. As already mentioned, the collection of the data for the production of the table can ensue continuously all day long, or data are communicated to the first computer 3 at a specific point in time after the end of the operation of the respective device.

In addition to the data of the devices MR1 through MR4 collected automatically via the communication network 1, the table can be supplemented by further, optionally prescribable data that are usually obtained from the devices in non-automated fashion. These include, for example, the acquisition price of a device or the operating costs of a device per day. The data can likewise be stored in the central data bank 2 via the first computer 3 or the simulation computer 4. Such data are usually user-specific data that are known only to and accessible to a particular person who would like to simulate the use of a system option for the person's own purposes.

Using a number of such tables compiled for individual calendar days, tables can be produced that contain data averaged over several days, weeks, months or years, particularly with respect to the usage data.

Based on the data compiled in such tables, various interested parties, for example the customer K, a distribution unit V, a development department E or a marketing department M of the manufacturer of the devices $G_1$ through $G_n$, can, using the simulation computer 4 or some other computer connected thereto, simulate various scenarios with respect to the use of an existing system option for one of the devices, or the use of a new system option that previously has not been present in the devices $G_1$ through $G_n$. The simulation program itself is installed on the simulation computer 4, which also can be connected to the Internet and function as a server. With a suitable enable signal, the simulation program can be implemented proceeding from arbitrary computers connected to the Internet, for example from the computers 5 through 8 allocated to the interested parties.

Based on the data of the table of FIG. 2 as well as additionally prescribed data about the operating costs, for example of the magnetic resonance device MR1 per day, the operator of the magnetic resonance device MR1 can, for example determine the examination costs per patient for the magnetic resonance apparatus MR1 and can compare those examination costs per patient to examination costs per patient of other operators of magnetic resonance devices. When, for example based on the operator's own operating costs, the operator of device MR1 sets up such a comparison to the examination per patient of the operator of magnetic resonance apparatus MR4, the operator of device MR1 will find that his operating costs per patient are higher than the operating costs per patient of the operator of the magnetic resonance apparatus MR4, who likewise mainly implements long and difficult examinations with the magnetic resonance apparatus MR4. It can be seen on the basis of the table that the magnetic resonance apparatus MR4—differing from the magnetic resonance apparatus MR1—additionally has a system option SO2 that is specifically provided for lung examinations, whereas the magnetic resonance apparatus MR1 only has the system option SO1 that is particularly provided for heart examinations but also allows lung examinations. Taking the system option SO2 into consideration, one can now simulate the extent to which the operator of the magnetic resonance apparatus MR1 can reduce the examination time per patient for lung examinations, which currently amounts to an average of fifty minutes. In particular, a determination can be made as to what extent the examination costs per patient can be reduced, taking the costs for the system option SO2 and the average the number of lung examinations into consideration, that are implemented with the magnetic resonance apparatus MR1 upon observation of a longer time span.

Moreover, the distribution department M of the manufacturer of the devices $G_1$ through $G_n$ can, using simulations of the user system options based on such tables, identify customers, i.e. device operators, who can be promised an improvement in workflow or profit when offered a specific system option. The development department E of the manufacturer of the devices $G_1$ through $G_n$ can recognize the necessity of new system options on the basis of simulations based on the tables and can develop such system options in targeted fashion and offer them to customers. The marketing department M of the manufacturer of the devices $G_1$ through $G_n$ can implement market analyses on the basis of the tables, and can estimate the market potential of new system options on the basis of simulations based on the tables.

It is thus clear that various scenarios for the use of a system option can be simulated and economic feasibility analyses can be implemented by means of the automated collection of data of apparatus in operation that are placed into relationship with one another as well as on the basis of additional, prescribable data.

In terms of its structure, the table shown in FIG. 2 is only an example. Thus, the table can include data for devices other than magnetic resonance apparatuses, for example x-ray computed tomography installations, so that, for example for identical examinations, the costs that are incurred given operation of a magnetic resonance apparatus can be compared to the costs that are incurred given operation of an x-ray computed tomography installation, and the use of various system options for the two different devices can be simulated and compared to one another.

Further, the standardized storage of the collected data need not necessarily ensue in the form of tables. Other known storage methods can be employed which allow a relationship between the collected data and the additionally prescribed data to be produced in a simple way.

Which data are collected is likewise optional. Thus, only configuration data, only usage data or only workflow data or any arbitrary combination of these data can be collected.

The simulation of the use of system options is thereby not limited to technical installations, devices and systems. The use of software system options can also be simulated with the inventive method.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for simulating a use of a system option for a technical apparatus, comprising the steps of:

operating at least one technical apparatus and collecting data as a result of said operation relating to at least one of configuration and usage of said apparatus;

storing the collected data in a central data bank as stored data;

prescribing additional data and storing said additional data in said central data bank as additional stored data;

identifying at least one relationship from relationships in the group consisting of relationships among said stored data and relationships between said stored data and said additionally stored data; and simulating operation of said at least one technical apparatus using a system option that is not physically present in said technical apparatus dependent on the data in said at least one relationship.

2. A method as claimed in claim 1 comprising filtering said collected data with regard to different data types, to obtain filtered data, and forwarding only said filtered data to said central data bank.

3. A method as claimed in claim 1 comprising automatically collecting said data.

4. A method as claimed in claim 1 comprising collecting said data via a communication network in communication with said technical apparatus.

5. A method as claimed in claim 1 wherein the step of collecting data during operation of a technical apparatus comprises collecting said data during operation of a medical technical apparatus.

6. A method as claimed in claim 5 comprising collecting said data from a medical technical apparatus selected from the group consisting of medical technical installations and medical technical devices.

7. A method as claimed in claim 5 comprising collecting said data from a medical technical apparatus selected from the group consisting of magnetic resonance apparatuses, computed tomography apparatuses, C-arm x-ray apparatuses, and ultrasound apparatuses.

* * * * *